US008388930B2

(12) United States Patent
Hillegonds et al.

(10) Patent No.: US 8,388,930 B2
(45) Date of Patent: *Mar. 5, 2013

(54) DIAGNOSIS AND ASSESSMENT OF SKELETAL RELATED DISEASE USING CALCIUM 41

(75) Inventors: Darren J. Hillegonds, Oakland, CA (US); John S. Vogel, San Jose, CA (US); Robert L. Fitzgerald, Encinitas, CA (US); Leonard J. Deftos, Del Mar, CA (US); David Herold, Del Mar, CA (US); Douglas W. Burton, San Diego, CA (US)

(73) Assignees: Lawrence LIvermore National Security, LLC, Livermore, CA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/448,045

(22) Filed: Apr. 16, 2012

(65) Prior Publication Data

US 2012/0225486 A1      Sep. 6, 2012

Related U.S. Application Data

(63) Continuation of application No. 11/283,034, filed on Nov. 17, 2005, now Pat. No. 8,178,076.

(60) Provisional application No. 60/629,354, filed on Nov. 18, 2004.

(51) Int. Cl.
*A61K 51/00* (2006.01)
*A61K 49/00* (2006.01)
*G01N 33/20* (2006.01)

(52) U.S. Cl. ............... 424/1.11; 424/9.1; 436/79
(58) Field of Classification Search .................. None
See application file for complete search history.

(56) References Cited

U.S. PATENT DOCUMENTS 5,209,919 A    5/1993   Turteltaub et al.
5,366,721 A    11/1994  Turteltaub et al.
5,376,355 A    12/1994  Turteltaub et al.

OTHER PUBLICATIONS

Vogel, J.S. Accelerator Mass Spectrometry as a Bioanalytical Tool; Sixth Symposium of the International Isotope Society, Philadelphia, PA, Oct. 1997.*
Wendt et al. Resonant Laser Ionization Mass Spectrometry: An Alternative to AMS?; Nuclear Instruments and Methods in Physics Research B, vol. 172 (2000) pp. 162-169.*
Cohn et al. The Spectrum of Metabolic Bone Disease in Lymphoblastic Leukemia; Cancer, vol. 59 (1987) pp. 346-350.*
Freeman, S.P.H.T., et al, "Biological Sample Preparation and 41Ca AMS Measurement at LLNL," Nuclear Instruments and Methods in Physics Research B, 99, (1995), pp. 557-561.
Fitzgerald, R.L., et al., "41Ca and Accelerator Mass Spectrometry to Monitor Calcium Metabolism in End Stage Renal Disease Patients," Clinical Chem., 51:11,(2005) pp. 2095-2102.
Elmore, D., et al., "Calcium-41 as a Long-term Biological Tracer for Bone Resorption," Nuclear Instruments and Methods in Physics Research B52, (1990), pp. 531-535.
Johnson, R.R., et al., "Calcium Resorption From Bone in a Human Studied by 41 Ca Tracing," Nucear Insuments and Metods in Physics Research B 92, (1994) pp483-488.
Hillegonds, D.J., et al., "High-throughput Measurement of 41Ca by Accelerator Mass Spectrometry to Quantitate Small Changes in Individual Human Bone Turnover Rates," JALA, (2004), pp. 99-102.
Freeman, S. P.H.T., et al, "Human Calcium Metabolism Including Bone Resporption Measured with 41Ca Tracer," Nuclear Instrumentation and Methods in Physics Research B 123 (1997), pp. 266-270.
Nishiizumi, K., et al, "Preparation of 41Ca AMS Standards," Nuclear Instruments and Methods in Physics Research B 172 (2000) pp. 399-403.
Lin, Y, et al., "Protocol for Assessing Bone health in Humans by Tracing Long-Lived 41Ca Isotope in Urine. Serum, and Saliva Samples," Analy. Biochem. 332 (2004) pp.193-195.
White, I. N.H., "Techniques: The Application of Accelerator Mass Spectrometry to Pharmacology and Toxicology," TRENDS in Pharmacoogical Sciences, vol. 25, No. 8, (2004), pp. 442-447.
Freeman, S. P.H.T., "The Study of Skeletal Calcium Metabolism with 41Ca and 45Ca," Nuclear Instruments and Methods in Physics Research B 172, (2000) pp. 930-933.

* cited by examiner

*Primary Examiner* — Rebecca Prouty
*Assistant Examiner* — Paul Martin
(74) *Attorney, Agent, or Firm* — Eddie E. Scott

(57) ABSTRACT

A method of determining calcium metabolism in a patient comprises the steps of administering radioactive calcium isotope $^{41}$Ca to the patient, allowing a period of time to elapse sufficient for dissemination and reaction of the radioactive calcium isotope $^{41}$Ca by the patient, obtaining a sample of the radioactive calcium isotope $^{41}$Ca from the patient, isolating the calcium content of the sample in a form suitable for precise measurement of isotopic calcium concentrations, and measuring the calcium content to determine parameters of calcium metabolism in the patient.

3 Claims, 4 Drawing Sheets

DIAGNOSIS AND ASSESSMENT OF SKELETAL RELATED DISEASE USING CALCIUM 41

CROSS-REFERENCE TO RELATED APPLICATIONS

The present application is a continuation of U.S. application Ser. No. 11/283,034, filed Nov. 17, 2005, entitled "DIAGNOSIS AND ASSESSMENT OF SKELETAL RELATED DISEASE USING CALCIUM 41", now U.S. Pat. No. 8,178,076; (meaning previous and current case not co-pending which is a non-provisional application of U.S. Provisional Application No. 60/629,354, filed Nov. 18, 2004, titled "Early diagnosis and assessment of skeletal-related disease using 41 Ca", the entire contents and disclosures of which are specially incorporated by reference herein.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to diagnosis and more particularly to diagnosis and assessment of skeletal related disease using calcium 41.

2. State of Technology

Skeletal complications of cancer cause significant health problems because certain tumors commonly metastasize to bone, including myeloma, breast, lung, prostate, kidney, thyroid, melanoma, and lymphomas. For these patients, skeletal complications such as intractable bone pain, pathologic fractures, nerve compression syndromes, and hypercalcemia signal that the malignant process is incurable (Mundy G R. Mechanisms of bone metastasis. Cancer. 1997; 80:1546-56). Cancer cells reaching the bone microenvironment hijack normal cellular function by producing bioactive factors and peptides, leading to osteosclerotic lesions and/or osteolytic bone destruction (Deftos L J. Prostate carcinoma: production of bioactive factors. Cancer. 2000; 88:3002-8). Accelerated bone turnover locally releases high concentrations of bone-derived growth factors, further promoting tumor growth in a vicious cycle (Mundy G R. Mechanisms of bone metastasis. Cancer. 1997; 80:1546-56).

The need for early detection and improved management of metastatic bone disease has driven the search for new markers of skeletal tumor burden, disease progression, and response to treatment (Vinholes J, Coleman R, Eastell R. Effects of bone metastases on bone metabolism: implications for diagnosis, imaging and assessment of response to cancer treatment Cancer Treat Rev. 1996; 22:298-331). Urinary and serum biomarkers of bone turnover, such as bone specific alkaline phosphatase and Type I collagen fragments, have proven useful in research populations (Coleman R E. The clinical use of bone resorption markers in patients with malignant bone disease. Cancer. 2002; 94:2521-33.), and may aid in directing treatment when greatly elevated (Brown J E, Cook R J, Major P, et al. Bone turnover markers as predictors of skeletal complications in prostate cancer, lung cancer, and other solid tumors. J Natl Cancer Inst. 2005; 97(459-69).

However, the ultimate value of these techniques for individual patients is uncertain, due (in part) to high natural variability of biomarkers in urine and serum (Kannis J A, McCloskey E V. Bone turnover and biochemical markers in malignancy. Cancer. 1997; 80:1538-45). Applicants believe that labeling the human skeleton with a $^{41}$Ca tracer and monitoring urinary tracer abundance will provide a non-invasive, highly sensitive, clinically useful measure of bone turnover. The longest half-life isotope of calcium, $^{41}$Ca, provides a sensitive method for tracking short and long-term bone turnover parameters. Due to extremely low natural abundance ($<10^{-15}$), a single sub-physiological $^{41}$Ca dose (less than 1 ug=4 kBq=0.1 uCi) remains quantifiable via accelerator mass spectrometry (AMS) in blood and urine for many years: this longevity within the body's primary calcium pool makes $^{41}$Ca variation specific to bone turnover (Weaver C M. Use of calcium tracers and biomarkers to determine calcium kinetics and bone turnover. Bone. 1998; 22(5):103S-104S). The long half-life (100,000 years) and low energy decay mode (pure electron capture) make $^{41}$Ca uniquely benign: lifetime radioactive exposure from ingested or injected dose (<2e-10 and <7e-10 Sv/Bq, respectively) is smaller than ten seconds of a commercial airline flight (Friedberg W, Copeland K, Duke F E, O'Brien K III, Darden E B Jr. Radiation exposure during air travel: guidance provided by the federal aviation administration for air carrier crews. Health Phys. 2000; 79(5):591-595). Applicants demonstrate that urinary $^{41}$Ca/Ca in humans is very stable over time, and that a $^{41}$Ca assay may be sensitive enough to detect modulations in urinary $^{41}$Ca/Ca due to bone disruption and tumor proliferation from metastatic bone disease. Applicants also conducted two proof-of-concept studies using a human xenograft tumor model in nude mice. One establishing that $^{41}$Ca preferentially labels bone, and another tested Applicants' hypothesis that pre-labeled bones release $^{41}$Ca at a rate directly proportional to cancer cell proliferation and bone destruction during robust skeletal tumor growth.

The article "high-throughput measurement of $^{41}$Ca by accelerator mass spectrometry to quantitate small changes in individual human bone turnover rates," by Darren J. Hillegonds, Robert Fitzgerald, David Herold, Yumei Lin, and John S. Vogel in the *Journal of the Association for Laboratory Automation (JALA)*, Volume 9, Issue 3, Pages 99-102 (June 2004) provides the following state of technology information, "Biochemical markers of bone turnover suffer from large analytical and natural fluctuations (20-30%), making small differences in bone resorption impossible to resolve. This limits the clinical utility of such markers for individuals with the skeletal complications associated with many disease states (e.g., metastatic cancer, renal failure, osteoporosis)."

The article "$^{41}$Ca and Accelerator Mass Spectrometry to Monitor Calcium Metabolism in End Stage Renal Disease Patients," by Robert L. Fitzgerald, Darren J. Hillegonds, Douglas W. Burton, Terrance L. Griffin, Scott Mullaney, John S. Vogel, Leonard J. Deftos, and David A. Herold in *Clinical Chemistry*, 2005; 51(11): 2095-2102 provides the following state of technology information, "Monitoring bone resorption with measurements of bone density and biochemical markers is indirect,"

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system for monitoring the progression or therapeutic regression of a disease that modifies bone turnover rates in a patient. In one embodiment the system comprising the steps of administering a dose of radioactive calcium isotope $^{41}$Ca to the patient at a time prior to the period in which the progression or therapeutic regression is to be observed, collection of bodily fluids from the patient at regular intervals during the period, isolating the calcium content of the sample in a form suitable for precise measurement of isotopic calcium concentrations, measuring the calcium content by an analytical system producing measurements, comparison of the measurements to a standard, and determination from the comparison any changes in the bone turnover rates within the period. The step of application of the determination to addressing the health status of the patient can be included.

In the step of comparison of the measurements to a standard, the standard can be similar samples from the patient, other persons who are in a similar state of health or disease, etc. the step of comparison of the measurements to a standard can comprise comparing the measurements to a compiled average behavior of the isotope concentrations in a suitable cohort of people, comparing the measurements to prior isotope concentrations in the patient, comparing the measurements to validated mathematical models of isotope concentration that have been demonstrated to reliably mirror known changes in bone turnover, etc.

In its broadest form the present invention provides a method of determining calcium metabolism in a patient comprising the steps of administering radioactive calcium isotope $^{41}$Ca to the patient, allowing a period of time to elapse sufficient for dissemination and reaction of the radioactive calcium isotope $^{41}$Ca by the patient, obtaining a sample of the radioactive calcium isotope $^{41}$Ca from the patient, isolating the calcium content of the sample in a form suitable for precise measurement of isotopic calcium concentrations, and measuring the calcium content to determine parameters of calcium metabolism in the patient. The step of allowing a period of time to elapse sufficient for dissemination and reaction of the radioactive calcium isotope $^{41}$Ca by the patient can be a time period of hours to years.

The present invention applies to any condition that perturbs calcium homeostasis. Uses of present invention include osteoarthritis, diabetes, and diseases that have deleterious effects on the kidney, liver, or gastrointestinal tract (because these affect vitamin D and calcium status). The present invention also facilitates vastly improved monitoring of calcium metabolic parameters when treatments for other conditions or diseases result in disruption of calcium metabolism (such as hormone therapies in peri- and post-menopause and hormone therapies common in prostate cancer treatments).

The present invention is useful in the management of osteoporosis in postmenopausal women not suffering from any other disease state. Medical application of the $^{41}$Ca assay can be significant, both for diagnosis, staging diseases after diagnosis, and in closely monitoring treatment efficacy. The $^{41}$Ca assay can be a valuable tool for the pharmaceutical industry in identifying at-risk populations among the larger research study populations, so as to allow testing of new drug candidates in the most appropriate subject populations. For example, testing a drug that halts early skeletal metastasis would currently involve a prohibitively large research subject population because it is currently difficult to make such an early diagnosis, and a large portion of the subject population would not develop skeletal metastases. Selecting a homogenous population in terms of calcium metabolism might also be required for research into drugs only tangentially related to calcium metabolism. The present invention is a valuable tool for the pharmaceutical industry in identifying at-risk populations among the larger research study populations, so as to allow testing of new drug candidates in the most appropriate subject populations.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
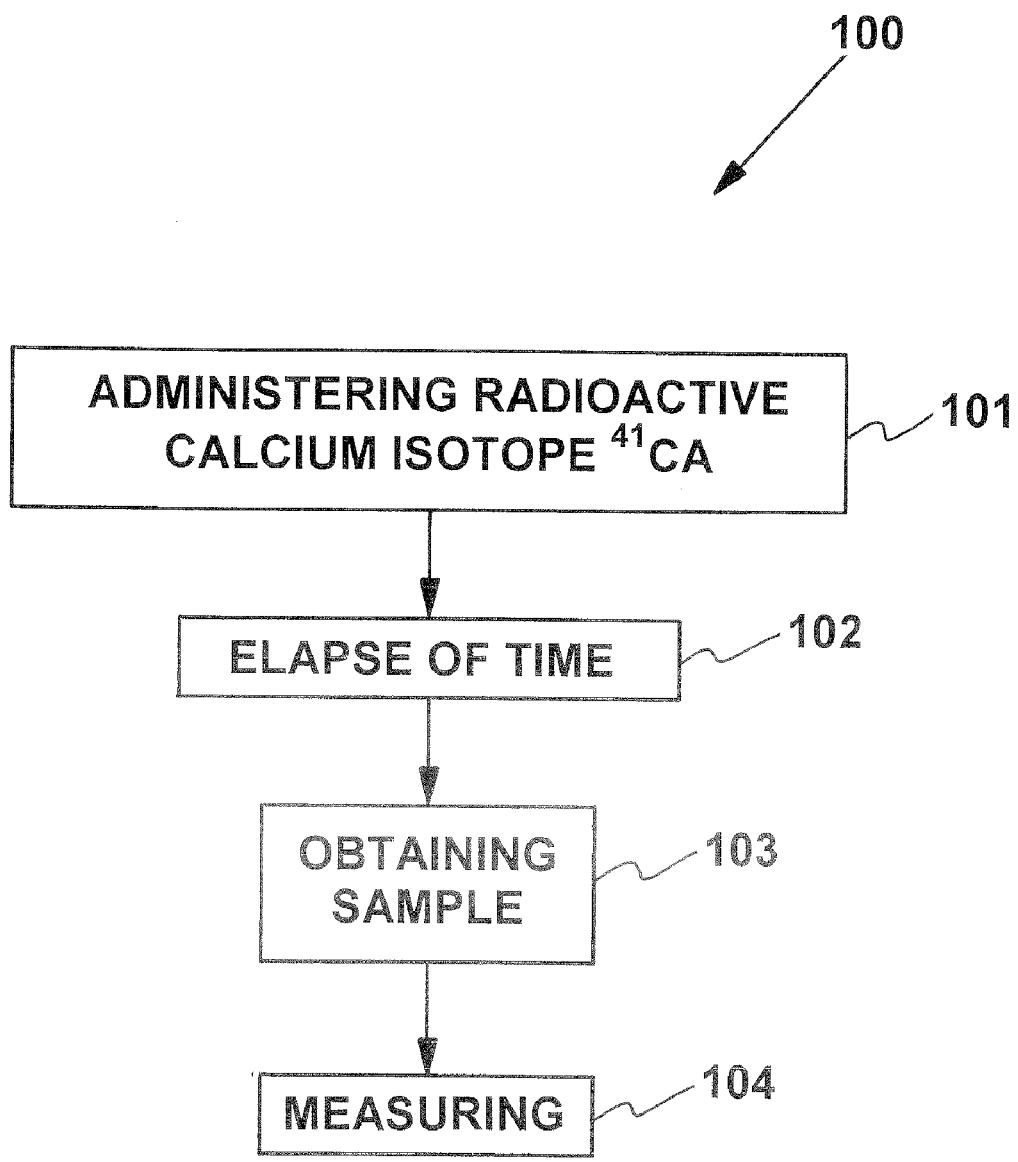
FIG. 1 is a flow chart that illustrates one embodiment of the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Throughout life, the living skeleton is successively broken down and reformed at rates depending on age, health, diet, exercise pattern, and other factors. Many diseases effect changes in skeletal turnover rates—osteoporosis is merely the best-known example. Medical science has long searched for improved methods of measuring bone strength and fracture risk. Currently, the best-studied clinical measurement of bone health is that of bone mineral density via x-ray analysis. X-ray analysis has severe limitations because of the generally slow rate of bone mass decreases, and changes are generally not significant until many months or years have passed. Nevertheless, bone mineral density (BMD) has been widely studied and is significantly correlated with fracture risk, which is the most clinically relevant manifestation of bone loss. Other imaging techniques such as computed tomography (CT) and micro-CT hold promise of looking not strictly at the compact bone (cortical) density but also at the internal structure and connectivity of the trabecular bone 'scaffolding'. Unfortunately, such imaging technologies require such significant effort from both the patient and the medical establishment (physicians, technicians) that they are not easily applied in routine patient care.

Another route of assessing bone turnover rate involves quantifying chemical signals present in the complex web of signaling pathways that control bone remodeling. For example, relatively high concentrations of osteoprotegrin (OPG) indicate that the body is correcting for faster than normal bone destruction—this chemical retards the pathway leading to formation of the cells that dissolve bone (called osteoclasts). Conversely, high levels of bone specific alkaline phosphatase (BSAP) indicate that the cells responsible for forming bone (osteoblasts) are more active than normal, indicating increased bone formation rate.

In addition to quantifying molecular pathways leading to bone turnover, the rate of bone destruction (a process called bone resorption) is directly relatable to the amount of molecular bone fragments present in urine and blood. These fragments are pieces of the most common protein in the body, collagen, which is a rigid rod-like structure that provides tensional strength to bones, holding them together while providing mechanical strength to bend and flex. Surrounding the collagen fibers is a mineral similar to marble, called hydroxyapatite, which is a made up of calcium phosphate crystals. The combination of collagen and hydroxyapatite is similar in function to reinforced concrete roadways, which would fall apart over time without steel bar reinforcement and deform under stress without hard cement. In a healthy adult, 1.5-2 grams of bone is destroyed every day and a similar amount is produced; in general, about 7% of the skeleton is being actively resorbed or formed at any given time. In order to distinguish between bone and non-bone collagen, assays quantify fragments of individual collagen 'rods' where one rod was linked to the next. Such cross-linked collagen residues assays are gaining wide acceptance as reliable markers of bone resorption rate, and have been applied in most studies where bone turnover is an important variable.

Notwithstanding high specificity, the day-to-day and person-to-person variability of all conventional bone turnover markers is fairly high (>20-30%), making them extremely insensitive. This inherent variability is minimized in research studies using large study populations or repeated measurements, but for individual diagnosis and clinical monitoring, existing methods are practically useless except in the most extreme cases. Nevertheless, without a viable alternative these markers continue to be discussed as clinical endpoints for diagnosis and treatment of skeletal disorders such as osteoporosis and metastatic bone disease, even while experts write that new laboratory tests for bone metabolism are urgently needed.

The present invention provides a $^{41}Ca$ assay that facilitates utilization of bone turnover rates clinically: unlike other methods of calcium metabolic quantitation, $^{41}Ca$ is extremely stable. Departures from the normal urinary or serum tracer content are easily quantified, making a new disease state or treatment efficacy immediately apparent.

Referring to the drawings, and in particular to FIG. 1, a flow chart that illustrates one embodiment of the present invention is shown. This embodiment of the present invention is designated generally by the reference numeral 100. The system 100 provides a method of determining calcium metabolism in a patient. The system 100 comprises the following steps. Step 101, administering radioactive calcium isotope $^{41}Ca$ to a patient. Step 102, allowing a period of time to elapse sufficient for dissemination and reaction of the radioactive calcium isotope $^{41}Ca$ by the patient. The step 102 of allowing a period of time to elapse sufficient for dissemination and reaction of said radioactive calcium isotope $^{41}Ca$ by the patient can be a time period of hours to years. Step 103, obtaining a sample of the radioactive calcium isotope $^{41}Ca$ from the patient. Step 104, measuring the radioactive calcium isotope $^{41}Ca$ to determine parameters of calcium metabolism in the patient.

Figure 2:
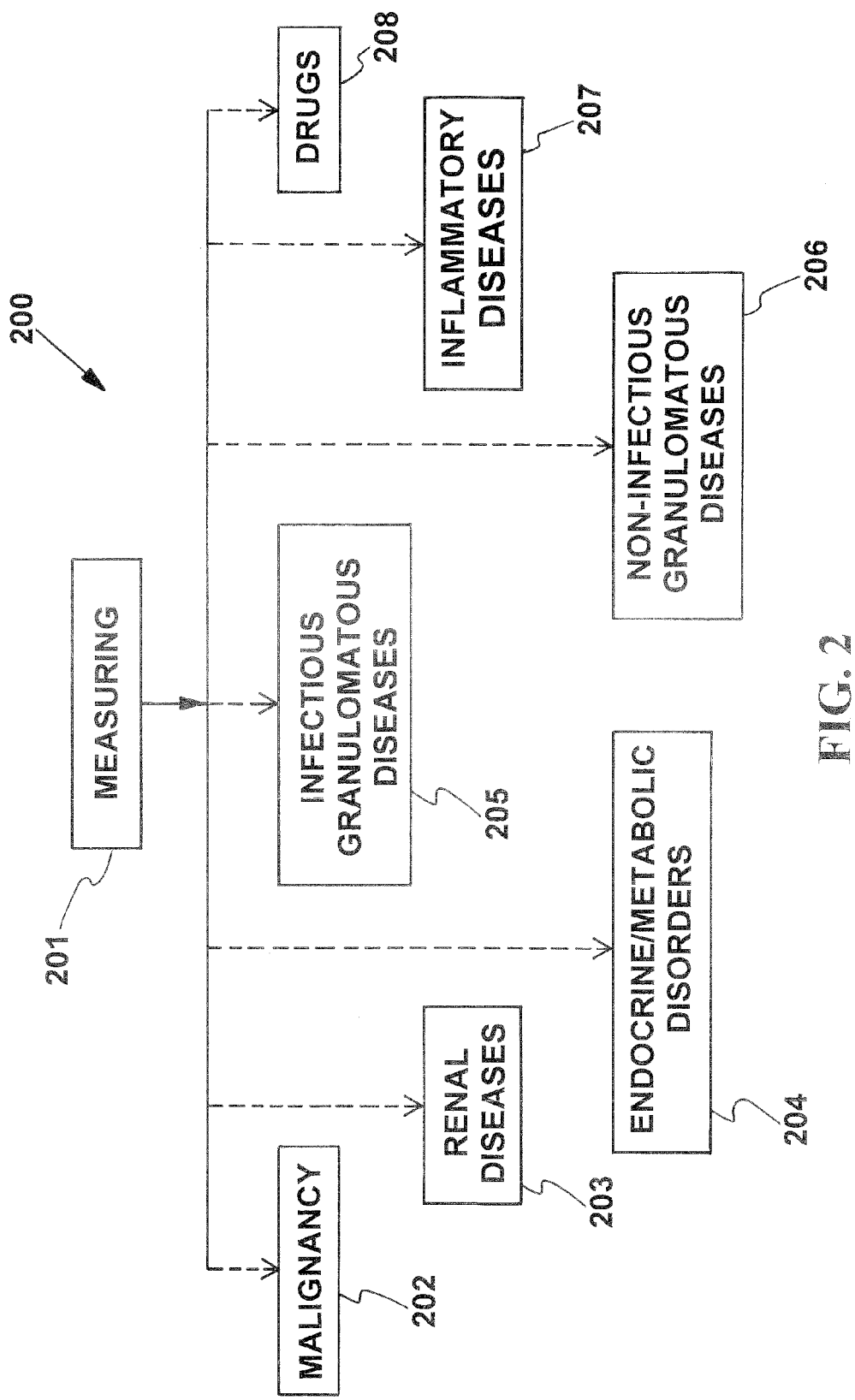
FIG. 2 provides additional information for the flow chart of FIG. 1.

Referring to FIG. 2, additional information for the Step 104, measuring the radioactive calcium isotope $^{41}Ca$ to determine parameters of calcium metabolism in the patient, of the flow chart of FIG. 1 is shown. The Step 104, measuring the radioactive calcium isotope $^{41}Ca$ to determine parameters of calcium metabolism can be applied to any condition that perturbs calcium homeostasis, in some cases resulting in hypercalcemia.

Steps 202 through 208 are illustrated in FIG. 2. Step 202, measuring malignancy, includes most solid tumors, hematological cancers such as myeloma, leukemia, and lymphoma. Step 203, measuring renal diseases, includes renal failure, tertiary hyperparathyroidism, states of immobilization, Paget's disease, whole body cast, zero gravity. Step 204, measuring endocrine/metabolic disorders, includes primary hyperparathyroidism, familial hypocalciuric hypercalcemia, William's syndrome, hyperthyroidism, hypoadrenalism, pheochromocytoma, vipoma, lactase deficiency, hypophosphatasia. Step 205, measuring infectious granulomatous diseases, includes sarcoidosis, coccidioidomycosis, cryptococcus, blastomyces, tuberculosis, histoplasmosis, leprosy, nocardia, candidiaisis, pneumocystis, bartonella, cytomegalovirus, and HIV/AIDS-associated diseases. Step 206, measuring non-infectious granulomatous diseases, includes silicone injections, talc, pulmonary eosinophilic granuloma, wegener granuloma, and berylliosis Step 207, measuring inflammatory diseases, includes systemic lupus erythematosis, acute rheumatic fever, richter's syndrome, crohn disease, and wegener granulaomatosis. Step 208, measuring drugs, includes vitamin D, vitamin A, calcium, milk alkali syndrome, dialysate calcium, lithium, manganese, thiazides, theophylline, tamoxifen, gangciclovir, growth hormone therapy, parenteral nutrition, and thyroid hormone excess.

Early detection and improved management of metastatic bone disease has driven the search for new markers of skeletal tumor burden, but existing techniques are insufficiently sensitive for routine clinical use. The present invention provides high precision assessment of skeletal remodeling using a $^{41}Ca$ tracer. The present invention will aid in clinical management of advanced cancer patients with osseous tumor growth, through timely, non-invasive staging, measurement of therapeutic success, and detection of progressive disease.

$^{41}Ca$ remains quantifiable via accelerator mass spectrometry (AMS) in human urine and blood for many years following a single chemically and radiologically benign oral or intravenous dose; this longevity makes urinary $^{41}Ca$ content very specific to bone turnover. Applicants assessed tracer uptake and $^{41}Ca/Ca$ variability in monthly urine samples for 700 days following a 1.2 ng oral $^{41}Ca$ dose in six human volunteers. $^{41}Ca/Ca$ scattered about individual linear fits by (5±3) % from days 500 to 700, making $^{41}Ca/Ca$ more stable than available bone formation or resorption markers (which vary by at least 10-30%). Applicants also measured tracer distribution and increased $^{41}Ca$ release from pre-labeled bones in a human xenograft model of metastatic bone disease from prostate cancer. Serum $^{41}Ca/Ca$ assessed bone destruction and demineralization in this animal model, positively correlating with tumor size, skeletal disruption, serum tumor markers, and degree of hypercalcemia. Low natural variability of urinary $^{41}Ca/Ca$ in humans will enable a non-invasive, highly sensitive clinical measure of bone turnover perturbations from metastatic bone disease.

Figure 3:
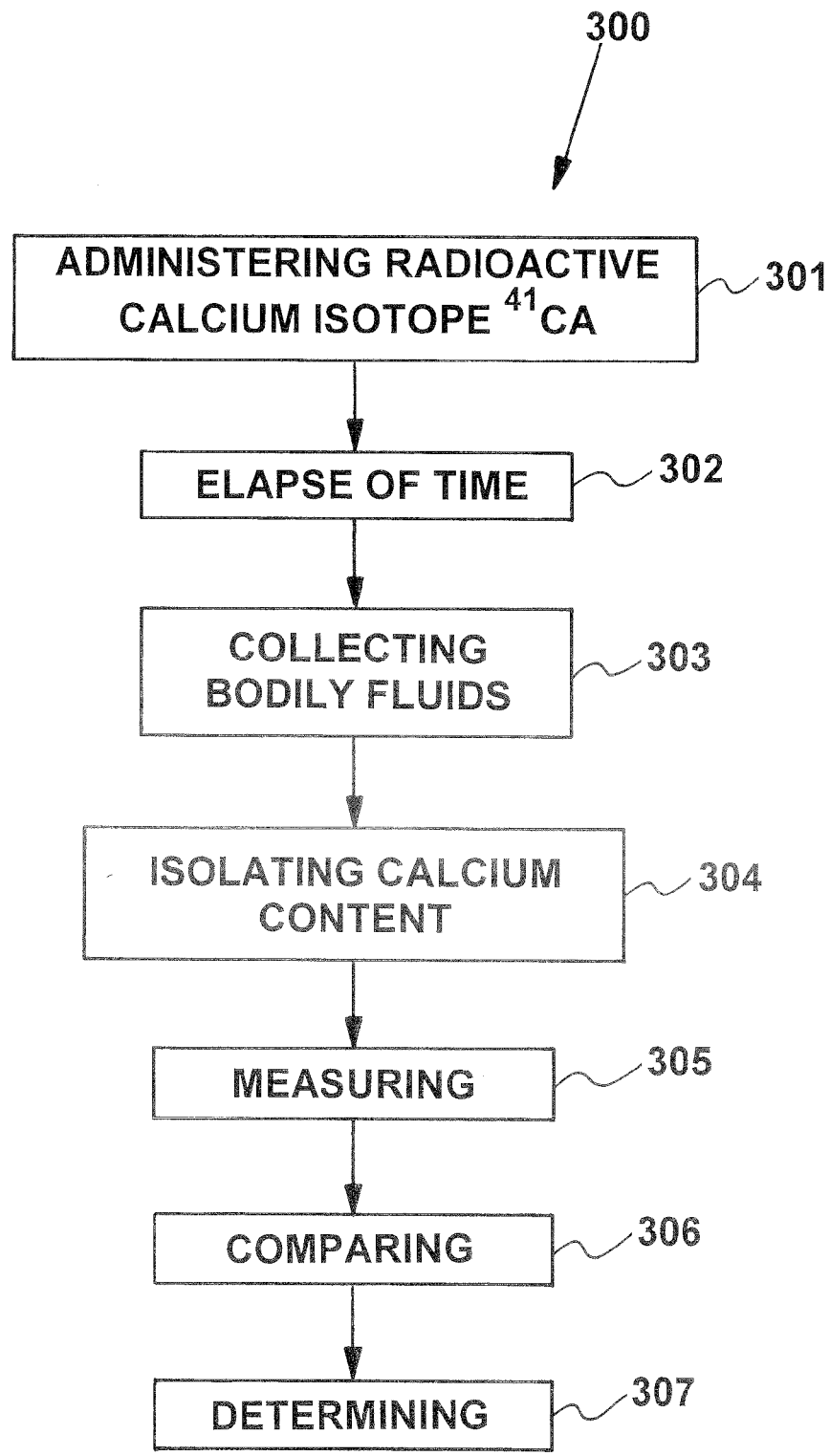
FIG. 3 is a flow chart that illustrates another embodiment of the present invention.

Referring to FIG. 3, a flow chart that illustrates another embodiment of the present invention is shown. This embodiment of the present invention is designated generally by the reference numeral 300. The system 300 provides a method of monitoring the progression or therapeutic regression of a disease that modifies bone turnover rates in a patient. The system 100 comprises the steps 301 through 307.

In step 301, a dose of radioactive calcium isotope $^{41}$Ca is administered to the patient at a time prior to the period in which the progression or therapeutic regression is to be observed. In step 302 a period of time is allowed to elapse. In step 303, bodily fluids are collected from the patient at regular intervals during the period. The bodily fluid may be, for example, urine, plasma, sweat, etc.

Step 304 comprises isolating the calcium content of the sample in a form suitable for precise measurement of isotopic calcium concentrations. In step 305 the calcium content is measured by an analytical system producing measurements. The analytical system may be, for example, accelerator mass spectrometry, resonance ionization mass spectrometry, atom trap trace analysis, decay counting, etc.

In step 306 the measurements are compared to a standard. The standard may be, for example, similar samples from the patient, other persons who are in a similar state of health or disease, etc. The comparison of measurements may be, for example, comparing the measurements to a compiled average behavior of the isotope concentrations in a suitable cohort of people, comparing the measurements to prior isotope concentrations in the patient, comparing the measurements to validated mathematical models of isotope concentration that have been demonstrated to reliably mirror known changes in bone turnover, etc.

Step 307 comprises determination from the comparison any changes in the bone turnover rates within the period. The step of application of the determination to addressing the health status of the patient may be included. Details of tests of the present invention are described in the article, "$^{41}$Ca and Accelerator Mass Spectrometry to Monitor Calcium Metabolism in End Stage Renal Disease Patients" by Robert L. Fitzgerald, Darren J. Hillegonds, Douglas W. Burton, Terrance L. Griffin, Scott Mullaney, John S. Vogel, Leonard J. Deftos, and David A. Herold in *Clinical Chemistry,* 2005; 51(11): 2095-2102. The article, "$^{41}$Ca and Accelerator Mass Spectrometry to Monitor Calcium Metabolism in End Stage Renal Disease Patients" by Robert L. Fitzgerald, Darren J. Hillegonds, Douglas W. Burton, Terrance L. Griffin, Scott Mullaney, John S. Vogel, Leonard J. Deftos, and David A. Herold in *Clinical Chemistry,* 2005; 51(11): 2095-2102, is incorporated herein by reference.

Figure 4:
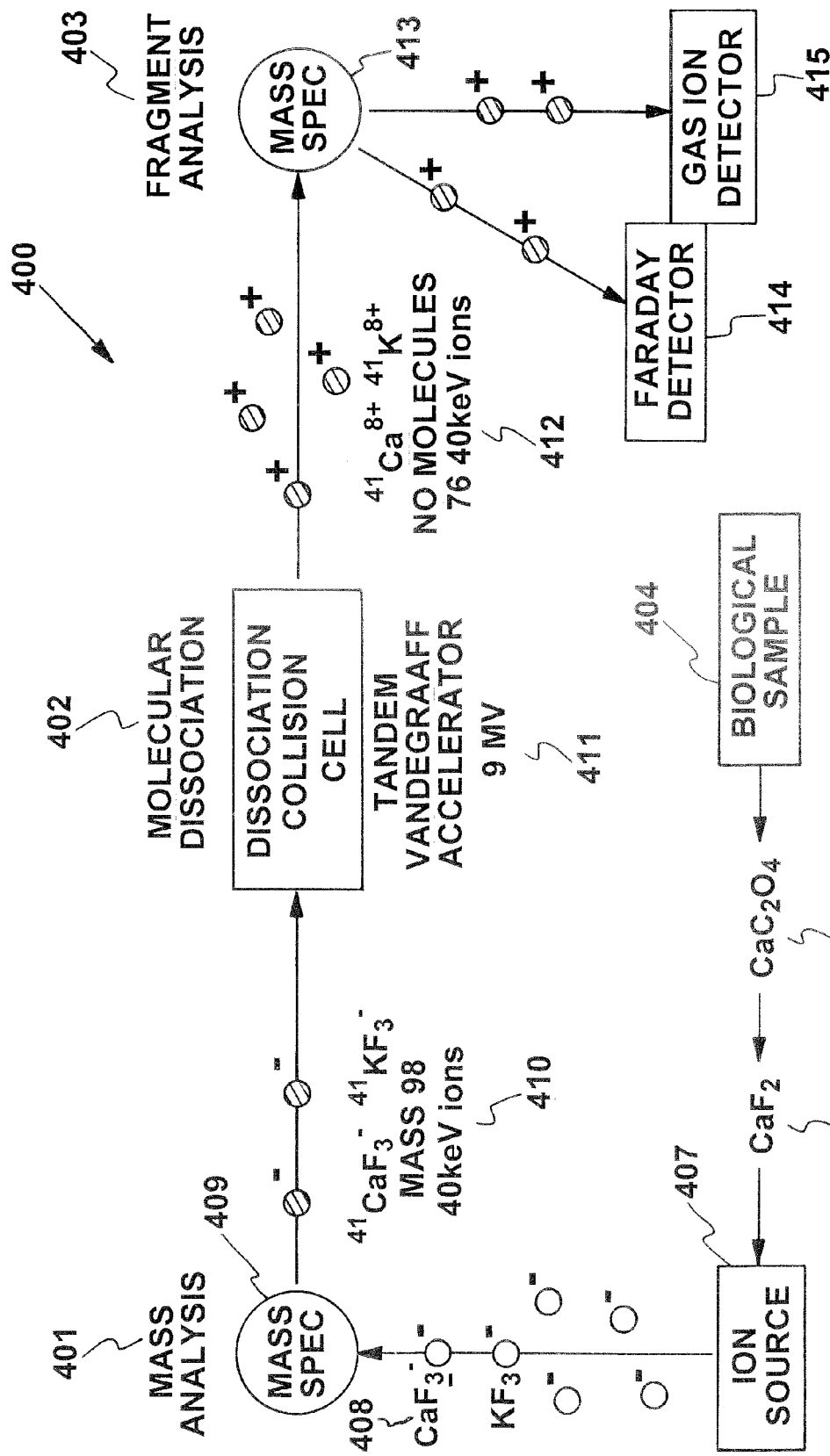
FIG. 4 is a schematic of an accelerator mass spectrometry system.

Referring to FIG. 4, additional information for the Step 104, measuring the radioactive calcium isotope $^{41}$Ca to determine parameters of calcium metabolism in the patient, of the flow chart of FIG. 1 is shown. In one embodiment, the step 104 of measuring the radioactive calcium isotope $^{41}$Ca to determine parameters of calcium metabolism in the patient comprises using an accelerator mass spectrometer (AMS) to measure the radioactive calcium isotope $^{41}$Ca to determine parameters of calcium metabolism in the patient. In another embodiment, the step 104 of measuring the radioactive calcium isotope $^{41}$Ca to determine parameters of calcium metabolism in the patient comprises using resonance ionization mass spectrometry (RIMS) to measure the radioactive calcium isotope $^{41}$Ca to determine parameters of calcium metabolism in the patient. In yet another embodiment, the step 104 of measuring the radioactive calcium isotope $^{41}$Ca to determine parameters of calcium metabolism in the patient comprises using atom trap trace analysis (ATTA) to measure the radioactive calcium isotope $^{41}$Ca to determine parameters of calcium metabolism in the patient.

FIG. 4 is a schematic of an accelerator mass spectrometry (AMS) system. The AMS system is designated generally by the reference numeral 400. The AMS system utilizes mass analysis 401, molecular dissociation 402, and fragment analysis 403. System for accelerator mass spectrometer (AMS) are described in U.S. Pat. No. 5,209,919; U.S. Pat. No. 5,366,721; and U.S. Pat. No. 5,376,355. U.S. Pat. No. 5,209,919; U.S. Pat. No. 5,366,721; and U.S. Pat. No. 5,376,355 are incorporated herein by reference.

In the mass analysis 401, a biological sample 404 is converted to $CaC_2O_4$, then CaF, and inserted into an ion source 407. The ions 408 are mass analyzed in a magnetic field 409. In the molecular dissociation 402, the mass 408 is sent to a dissociation collision cell 411. The AMS 41Ca measurements are accomplished via: (A) mass separation of $CaF^{3-}$ molecules, (B) acceleration of these molecules through 9 million volts, (C) removal of nine electrons through charge exchange in a thin carbon foil at the high-voltage terminal (thus destroying all molecular interferences), (D) a second stage of acceleration to ground potential, (E) fragment mass analysis, (F) measurement of $^{40}Ca^{8+}$ in an offset Faraday cup, and (G) ion identification and single particle counting of $^{41}Ca^{8+}$ in a multianode gas ionization detector. Applicants' analytical $^{41}$Ca/Ca background level is 2×10×14. Applicants' limit of quantitation is $^{41}$Ca/Ca-1×10$^{-13}$, which equates to about 0.01 fmol 41Ca per 25 mL urine or 2.5 mL plasma.

Measurement precision is monitored using secondary standards similar in isotope ratio to unknowns, and is currently ±3%, assuming sufficient sample $^{41}$Ca content to identify at least 1,000 $^{41}$Ca ions. Sample processing involves selective precipitation (as calcium oxalate) and ion exchange purification of Ca, followed by calcium fluoride production using HF.1.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of measuring calcium metabolism in a patient and obtaining information useful for determining the effect of drugs in the patient, comprising the steps of:

administering radioactive calcium isotope $^{41}$Ca to the patient, allowing a period of time to elapse sufficient for dissemination and reaction of said radioactive calcium isotope $^{41}$Ca by the patient, obtaining a sample of said radioactive calcium isotope $^{41}$Ca from the patient, isolating the calcium content of said sample in a form suitable for precise measurement of isotopic calcium concentrations, measuring said isotopic calcium concentrations of said calcium thereby producing measurements of parameters of calcium metabolism, wherein said step of measuring said isotopic calcium concentrations to determine parameters of calcium metabolism in the patient comprises using decay counting to measure said radioactive calcium isotope $^{41}$Ca to determine parameters of calcium metabolism in the patient, and obtaining the information useful for determining the effect of drugs in the patient by comparing said measurements of parameters of calcium metabolism to a standard, wherein said step of obtaining the information useful for determining the effect of drugs in the patient by comparing said measurements of parameters of calcium metabolism to a standard includes obtaining the information useful for determining the effect of drugs in the patient by comparing said measurements of parameters of calcium metabolism to a standard of parameters of calcium metabolism for average patients administered said drugs.

2. A method of monitoring the progression or therapeutic regression of a disease that modifies bone turnover rates in a patient, comprising the steps of:

administering a dose of radioactive calcium isotope $^{41}$Ca to the patient at a time prior to the period in which the progression or therapeutic regression is to be observed, allowing a period of time to elapse sufficient for dissemination and reaction of said radioactive calcium isotope $^{41}$Ca by the patient, collection of bodily fluids from the patient at regular intervals during said period of time wherein said step of collection of bodily fluids from the patient comprises collecting urine and sweat from the patient isolating the calcium content of said urine and sweat samples in a form suitable for precise measurement of isotopic calcium concentrations, measuring said isotopic calcium concentrations of said calcium by an analytical system producing measurements, comparing of said measurements to a standard, and determination from said comparison any changes in the bone turnover rates within said period.

3. A method of monitoring the progression or therapeutic regression of a disease that modifies bone turnover rates in a patient, comprising the steps of:

administering a dose of radioactive calcium isotope $^{41}$Ca to the patient at a time prior to the period in which the progression or therapeutic regression is to be observed, allowing a period of time to elapse sufficient for dissemination and reaction of said radioactive calcium isotope $^{41}$Ca by the patient, collection of bodily fluids from the patient at regular intervals during said period of time wherein said step of collection comprises collecting sweat, isolating the calcium content of said sweat sample in a form suitable for precise measurement of isotopic calcium concentrations, measuring said isotopic calcium concentrations of said calcium by an analytical system producing measurements, wherein said step of measuring said calcium content by an analytical system comprises measuring said calcium content by decay counting, comparing of said measurements to a standard, and determination from said comparison any changes in the bone turnover rates within said period.

* * * * *